United States Patent
Havkin-Frenkel et al.

(10) Patent No.: US 7,226,783 B1
(45) Date of Patent: Jun. 5, 2007

(54) VANILLIN PRODUCTION

(75) Inventors: Daphna Havkin-Frenkel, North Brunswick, NJ (US); Andrzej Podstolski, Warsaw (PL)

(73) Assignee: David Michael & Co., Inc., Philadelphia, PA (US)

( * ) Notice: Subject to any disclaimer, the term of this patent is extended or adjusted under 35 U.S.C. 154(b) by 0 days.

(21) Appl. No.: 09/462,576

(22) PCT Filed: Jul. 15, 1998

(86) PCT No.: PCT/US98/14895

§ 371 (c)(1),
(2), (4) Date: May 25, 2000

(87) PCT Pub. No.: WO99/03975

PCT Pub. Date: Jan. 28, 1999

Related U.S. Application Data (60) Provisional application No. 60/052,606, filed on Jul. 15, 1997.

(51) Int. Cl.
*C12N 5/04* (2006.01)

(52) U.S. Cl. .................... 435/410; 435/420; 435/430.1

(58) Field of Classification Search ................ 435/410, 435/420, 430.1
See application file for complete search history.

(56) References Cited

U.S. PATENT DOCUMENTS 5,057,424 A * 10/1991 Knuth et al. ................. 435/410
5,279,950 A    1/1994 Labuda
5,552,307 A    9/1996 Kessler
5,656,482 A    8/1997 Knorr

FOREIGN PATENT DOCUMENTS

WO        WO 99/03975 A1    1/1999

OTHER PUBLICATIONS

Rao et al, Vanilla flavour: production by conventional and biotechnological routes, Journal of the Science of Food and Agriculture, 2000, vol. 80, pp. 289-304.*
Yin et al. Incomplete factorial and response surface methods in experimental design: yield optimization of tRNATrp from in vitro T7 RNA polymerase transcription. Nucleic Acids Research, 1996, vol. 24, pp. 1279-1286.*
Rao SR et al. Vanilla flavour: production by conventional and biotechnological routes. J. Sci Food Agric 80: 289-304 (2000).*
Havkin-Frenkel, D., Dorn, R. and Leustek, T. Plant Tissue Culture for Production of Secondary Metabolites. *Food Technology.*. 1997. 51(11):56-58,61. USA.
Risch, S.J. and Ho, C-T. Spices Flavor Chemistry and Antioxidant Properties. *ACS Symposium Series 660*. 1996. 30-39. *American Chemical Society* USA.
Funk, C. and Brodelius, P.E.. Phenylopropanoid Metabolism in Suspension Cultures of *Vanilla planifolia* Andr.: Effects of Precursor Feeding and Metabolic Inhibitors. *Plant Physiol.* 1990. 94. 95-101.
Funk, C. and Brodelius, P.E.. Phenylopropanoid Metabolism in Suspension Cultures of *Vanilla planifolia* Andr.: Conversion of 4-Methoxycinnamic Acids into 4-Hydroxybenzoic Acids. *Plant Physiol.* 1990. 94. 102-108.
The PCT International Search Report dated Nov. 5, 2003 (PCT/US03/06397).

* cited by examiner

*Primary Examiner*—Cynthia Collins
(74) *Attorney, Agent, or Firm*—Drinker Biddle & Reath (57) ABSTRACT

Novel compositions and methods for improving vanillin production in cultured *Vanilla planifolia* and in intact plants are provided. Transgenic cells and plants having improved vanillin production are also provided.

11 Claims, 3 Drawing Sheets

VANILLIN PRODUCTION

This application claims priority to U.S. Provisional Application No. 60/052,606, filed Jul. 15, 1997, which is incorporated herein by reference in its entirety.

FIELD OF THE INVENTION

This invention relates to the field of plant tissue culture and plant genetic engineering to improve agronomic or commercial properties of plants. In particular, this invention provides novel compositions, methods and transgenic cells and plants of *Vanilla planifolia*, for the improved production of vanillin.

BACKGROUND OF THE INVENTION

Vanillin is the major principle flavor ingredient in vanilla extract and is also noted as a nutraceutical because of its anti-oxidant and antimicrobial properties. Vanillin can be used as a masking agent for undesirable flavors of other nutraceuticals. Vanilla extract is obtained from cured vanilla beans, the bean-like pod produced by *Vanilla planifolia*, a tropical climbing orchid.

Vanilla extract is widely used as a flavor by the food and beverage industry, and is used increasingly in perfumes. The U.S. annual consumption of vanilla beans, all of which are imported from foreign countries, is 1,200–1,400 tons, with a market value of about $100 million. By FDA definition, vanillin can be labeled as natural only when it is derived from vanilla beans. Currently, natural vanilla obtained through extraction of vanilla beans as described below, costs between $1,500 and $3,000 per kilogram. Vanillin is also produced by molecular breakage of curcumin, eugenol or piperin at a cost of $1,000/kg or less. However, vanillin produced by this method can be labeled as a natural flavor only in non-vanilla flavors. Vanillin chemically synthesized from guaiacol is consumed at a rate of about 800 tons per year in the United States for the food and beverage industry, at a cost of production of about $15/kg.

Natural vanilla extract currently produced from vanilla beans is presently the most desirable form of vanilla, due to the recent demand for natural food ingredients. The areas of the world capable of supporting vanilla cultivation are limited, due to its requirement for a warm, moist and tropical climate with frequent, but not excessive rain, and moderate sunlight. The primary growing region for vanilla is around the Indian Ocean, in Madagascar, Comoros, Reunion and Indonesia.

The production of vanilla beans is a lengthy process that is highly dependent on suitable soil and weather conditions. Beans (pod-like fruit) are produced after 4–5 years of cultivation. Flowers must be hand-pollinated, and fruit production takes about 8–10 months. The characteristic flavor and aroma develops in the fruit after a process called "curing," lasting an additional 3–6 months. For a complete review of the vanilla growing and curing process, see D. Havkin Frenkel & R. Dorn, "Vanilla," Chapter 4 in *Spices: Flavor Chemistry and Antioxidant Properties*, (Eds. Risch & Ho), American Chemical Society, Washington, 1997.

Interest has focused recently on plant cell and tissue culture as an approach to control quality and yield of vanilla production and to solve some of the agronomic problems associated with growing vanilla. Plant tissue culture should be useful for three objectives: (1) micropropagation of vanilla plants; (2) production of vanillin and other secondary products associated with vanilla flavor; and (3) improving production of vanillin in culture or in intact plants by elucidating and manipulating the biosynthetic pathways of vanillin and other flavor compounds. In connection with this last objective, efforts have been made to commercialize production of vanillin, the most valuable component of vanilla, by using plant cell culture. However, these efforts have not resulted in economically significant amounts of vanillin production, perhaps due in part to the heretofore incomplete understanding of the vanillin biosynthetic pathway.

From the foregoing, it can be seen that improvement of vanillin production, either in tissue culture or in intact plants, would be of significant agronomic and economic advantage. Accordingly, it is an object of this invention to provide means for obtaining high yields of vanillin from cultured cells and tissues. It is another object of this invention to improve vanillin production in intact vanilla plants.

SUMMARY OF THE INVENTION

Novel compositions and methods for improving vanillin production in cultured *Vanilla planifolia* and in intact plants are provided. These cultures and plants are expected to be of significant agronomic and economic value.

According to one aspect of the invention, a method for improving production of vanillin in cultured *Vanilla planifolia* is provided. The method comprises supplementing the culture with a compound selected from the group consisting of malic acid, 3,4-dihydroxybenzaldehyde, citric acid, pyruvic acid, oxaloacetic acid, succinic acid, glycosylated lysozyme, and any combination thereof, in an amount effective to improve the vanillin production as compared with cultures not supplemented with the compound.

In preferred embodiments of the invention, the tissue culture is an embryo culture. In another preferred embodiment, the culture is supplemented with malic acid at a concentration of between about 0.01% and 5% by weight of the culture medium. In another preferred embodiment, the culture is supplemented with 3,4-dihydroxybenzaldehyde at a concentration of between about 0.1 and 5 mM. In another embodiment, the culture is supplemented with about 0.01 to about 5% by weight of a compound selected from the group consisting of succinic acid, oxaloacetic acid, citric acid and pyruvic acid. In yet another embodiment, the culture is supplemented with about 1 to about 100 µg/ml of glycosylated lysozyme.

According to another aspect of the invention, cultured *Vanilla planifolia* cells, produced by the aforementioned method, are provided. These cells preferably produce at least twice as much vanillin as equivalent cultured cells not supplemented with the listed compounds.

In an particularly preferred embodiment the cells produce at least ten times, and most preferably 50 to 100 times, as much vanillin as equivalent cultured cells not supplemented with the compounds.

According to another aspect of the invention, a second method for improving production of vanillin in cultured *Vanilla planifolia* is provided. This method comprises subjecting the culture to a stress condition selected from the group consisting of heat stress and mechanical shear stress, in an amount and for a time effective to improve the vanillin production as compared with cultures not subjected to the stress condition. In a preferred embodiment, the heat stress comprises maintaining the cultures between about 33 and 37° C. for between three and seven days. In another embodiment, the mechanical shear stress is imposed by placing the cultures in an impeller-driven incubator, under conditions whereby the shear stress is caused.

Cultured *Vanilla planifolia* cells produced by the aforementioned method are also provided. In a preferred embodiment, these cells produce at least twice as much vanillin as equivalent cultured cells not subjected to the stress.

According to another aspect of the invention, a method for improving vanillin production in *Vanilla planifolia*, is provided, which comprises genetically engineering the *Vanilla planifolia* to overproduce one or more enzymes associated with one or more steps of vanillin biosynthesis in the *Vanilla planifolia*. The steps are selected from the group consisting of: chain shortening of p-coumaric acid to p-hydroxybenzaldehyde; chain shortening of ferulic acid to vanillin; hydroxylation of p-hydroxybenzyl alcohol to 3,4-dihydroxybenzyl alcohol or aldehyde; and methylation of 3,4-dihydroxybenzaldehyde to vanillin. The enzymes preferably are selected from the group consisting of: at least one p-hydroxybenzaldehyde synthase; at least one cytochrome p450 monooxygenase; and at least one methyl transferase.

In one embodiment of the aforementioned method, the genetically engineered *Vanilla planifolia* is a cell or tissue culture. In another embodiment, it is a whole plant. Genetically engineered *Vanilla planifolia* cells or plants produced by the aforementioned method are also provided.

These cells or plants preferably produce at least twice as much vanillin as does an equivalent cell which is not comparably genetically engineered.

According to yet another aspect of the invention, a method for improving vanillin accumulation in cell or tissue culture of *Vanilla planifolia* is provided, which comprises inhibiting production or activity of vanillyl alcohol dehydrogenase in cells comprising the cell or tissue culture, the inhibition resulting in the improved vanillin accumulation. In one embodiment, the inhibiting comprises genetically engineering the cells to inhibit expression of a gene encoding the vanillyl alcohol dehydrogenase. In another embodiment, the inhibiting comprises treating the culture with an inhibitor of vanillyl alcohol dehydrogenase activity. Cultures produced by the aforementioned method are also provided.

According to still another aspect of the present invention, a method for improving vanillin production and accumulation in a *Vanilla planifolia* cell or tissue culture is provided, which comprises: (a) genetically engineering the *Vanilla planifolia* to overproduce one or more enzymes associated with one or more steps of vanillin biosynthesis in the *Vanilla planifolia*, the steps selected from the group consisting of: chain shortening of p-coumaric acid to p-hydroxybenzaldehyde; chain shortening of ferulic acid to vanillin; hydroxylation of p-hydroxybenzyl alcohol to 3,4-dihydroxybenzyl alcohol or aldehyde; and methylation of 3,4-dihydroxybenzaldehyde to vanillin, thereby resulting in the improved vanillin production; and (b) inhibiting production or activity of vanillyl alcohol dehydrogenase in cells of the culture, thereby resulting in the improved vanillin accumulation. A *Vanilla planifolia* cell or tissue culture produced by the aforementioned method is also provided.

Additional features and advantages of the present invention will be understood by reference to the drawings, detailed description and examples that follow.

DETAILED DESCRIPTION OF THE INVENTION

I. Definitions

Various terms relating to the biological molecules of the present invention are used hereinabove and also throughout the specification and claims. The terms "substantially the same," "percent similarity" and "percent identity" are defined in detail below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules of the invention the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to oligonucleotides or hybridization generally, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the 5' regulatory regions of a gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. Other methods of delivery such as *Agrobacterium* T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

II. Description

In an effort to obtain commercially feasible tissue culture yields of vanillin and related compounds, the inventors have now elucidated the biosynthetic pathway by which these compounds are produced out of several possible pathways which have been proposed, and have determined the rate-limiting step in the biosynthesis. The important discovery of the correct pathway, and the rate limiting step in particular, has contributed to the development of high-yield tissue culture for vanillin production.

Another important feature of the present invention is the use of embryo cultures of vanilla plants for the purpose of producing vanillin at an economically feasible level. Embryo culture of *Vanilla planifolia* is described in detail in Example 1.

Figure 1:
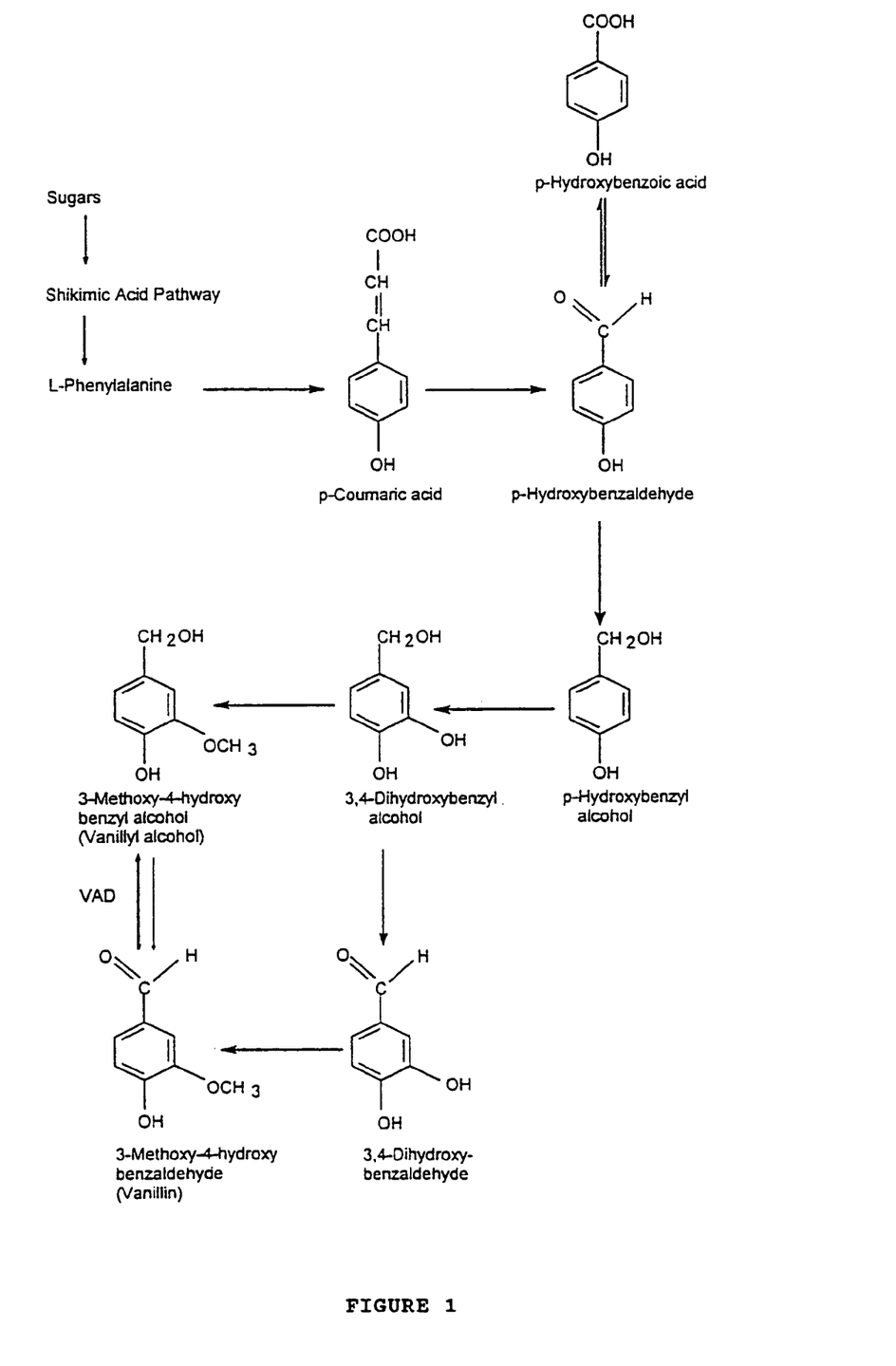
FIG. 1. Schematic diagram showing the biosynthetic pathway of vanillin in *Vanilla planifolia*.

The vanillin biosynthetic pathway is shown in FIG. 1 and described in detail in Example 2. As can be seen from FIG. 1, p-coumaric acid is produced from L-phenylalanine via the shikimic acid pathway. The first key step in the pathway is the chain shortening of p-coumaric acid to form p-hydroxybenzyaldehyde, then p-hydroxybenzyl alcohol. The next key step is the hydroxylation of p-hydroxybenzyl alcohol to 3,4-dihydroxybenzyl alcohol, then 3,4-dihydroxybenzaldehyde (sometimes referred to herein as "proaldehyde"). This is believed to be the rate limiting step in the pathway. Proaldehyde is next methylated to form vanillin (3-methoxy-4-hydroxybenzaldehyde). In cultured cells, much of the vanillin produced is reduced to vanillyl alcohol, which is a detrimental occurrence inasmuch as it depletes the culture of accumulated vanillin.

The enzymes involved in the vanillin biosynthetic pathway are believed to be the following. The chain shortening of p-coumaric acid to form p-hydroxybenzaldehyde is catalyzed by at least one chain-shortening enzyme, sometimes referred to herein as p-hydroxybenzaldehyde synthase. The partial purification and characterization of a p-hydroxybenzaldahyde synthase from *V. planifolia* is described in Example 6.

The enzyme catalyzing the rate-limiting hydroxylation of p-hydroxybenzyl alcohol to 3,4-dihydroxybenzyl alcohol is believed to be a cytochrome P450 monooxygenase. Strategies for cloning the gene(s) encoding the enzyme(s) are described in greater detail below and in Example 7.

The enzyme catalyzing the methylation of 3,4-dihydroxybenzaldehyde to vanillin has been determined to be an O-methyltransferase. This methyl transferase may be purified from cultured vanilla cells or from intact plants, according to one of several methods available in the art for purifying O-methyl transferase. In a preferred embodiment, it is purified according to the method of Edwards & Dixon, Arch. Biochem. Biophys. 287: 372–379, 1991.

The enzyme catalyzing the conversion of vanillin to vanillyl alcohol has been determined to be an alcohol dehydrogenase, which the inventors have named vanillyl alcohol dehydrogenase (VAD). The purification of VAD from cultured cells of *V. planifolia* and its characterization are described in Example 8.

In the present invention, two general approaches are used to improve vanillin production in cultured cells and, in some instances, in intact vanilla plants. The first approach employs manipulation of tissue culture conditions to increase vanillin accumulation in cultured cells. The second approach employs genetic manipulation of the vanillin biosynthetic pathway by up-regulating or down-regulating, as appropriate, enzymes involved in the vanillin biosynthetic pathway or in the conversion of vanillin to vanillyl alcohol. These approaches are described below.

A. Improving Vanillin Production in Tissue Culture by Manipulation of Culture Conditions It has been discovered in accordance with the invention that addition of certain "elicitor" compounds provides a surprisingly high yield of vanillin and related compounds in plant tissue culture, particularly embryo culture. These elicitor compounds include malic acid, citric acid, succinic acid, pyruvic acid and oxaloacetic acid. No method heretofore described has employed these compounds in plant tissue culture to stimulate production of vanillin and similar compounds.

Malic acid is especially successful in this respect. The use of malic acid in an amount effective to increase production of vanillin and related compounds in plant tissue is an important part of the present invention. Malic acid may be used with any type of plant tissue, under any form of cultivation or in any conditions known for plant tissue culture. For instance, Table 6 in Example 5 shows that 3% malic acid used in elicitation of embryo cultures increases vanillin yield from 5 to 72 mg/100 g tissue. Citric acid, succinic acid, pyruvic acid and oxaloacetic acid may also be used in amounts effective to increase yields of vanillin and related compounds at least two- three-fold in plant tissue culture, such as at about 0.1% to about 5.0%, preferably from about 0.5 to 3.0%, and otherwise as discussed for malic acid here and in the Examples.

Another useful elicitor of vanillin production in cultured vanilla is glycosylated lysozyme, a protein elicitor described in U.S. Pat. No. 5,552,307 to Kessler et al. As shown in Example 5, treatment with this elicitor more than doubles the amount of vanillin produced in cultured vanilla cells.

Another elicitor of vanillin production in cultured cells is heat stress, i.e. placing the cultures at 33–37° C. for an extended period of time. Heat stress of this nature has been found to increase production of vanillin and related compounds in cultured cells by at least 2–3 fold. Similarly, shear stress, as described in greater detail in the examples, increases production of vanillin and related compounds in cultured cells by at least 2–3 fold.

Also in accordance with the present invention, vanillin production in cultured cells may be improved by feeding the cultures with an excess of any of the precursors or intermediates in the vanillin biosynthetic pathway. For instance, proaldehyde (3,4-dihydroxybenzaldahyde, the immediate precursor of vanillin) can be used with any type of plant tissue under any form of cultivation or any conditions known for plant tissue culture to stimulate vanillin synthesis. A proaldehyde concentration of 0.1 to 5.0 mM is especially useful. Examples of specific conditions for addition of proaldehyde are set forth in Example 3. Furthermore, Example 3 also describes that precursors can be fed to intact green vanilla beans to improve vanillin production in the beans.

B. Improving Vanillin Production in Tissue Culture and Intact Plants by Manipulation of Enzymes of the Vanillin Biosynthetic Pathway Manipulation of the enzymes involved in the vanillin biosynthetic pathway is another approach used in accordance with this invention to improve vanillin production in vanilla tissue culture and in intact plants. As discussed below and in the examples, the inventors have either isolated these enzymes or devised means for their isolation using standard methodologies known in the art, as described in greater detail in the Examples. These enzymes may be added to or inhibited in plant cultures directly, or plant tissues may be engineered for altered expression of the genes encoding the enzymes, by one of several methods as described below.

The first key enzyme in the vanillin biosynthetic pathway is the enzyme referred to herein as the "chain shortening enzyme" or p-hydroxybenzaldehyde synthase, which catalyzes the conversion of p-coumaric acid to p-hydroxybenzaldehyde. Though the chain shortening enzyme may be referred to in the singular, it is possible that this activity is performed by more than one enzyme. The conversion of p-coumaric acid to p-hydroxybenzaldehyde is not considered to be the rate-limiting step in vanillin biosynthesis in cultured cells. However, it may play a more important rate-controlling function in intact vanilla beans. In either case, it is believed that up-regulation or some other form of supplementation of this enzyme will enhance vanillin production in cultured cells and in intact plants.

Another chain shortening enzyme that is expected to be useful for practice of the invention is the chain-shortening enzyme(s) that catalyze the conversion of ferulic acid to vanillin. These enzymes may be used in conjunction with a growth medium containing ferulic acid, to stimulate production of vanillin.

The next key enzyme in the vanillin biosynthetic pathway is the oxygenase that catalyzes hydroxylation of p-hydroxybenzyl alcohol to 3,4-dihydroxybenzyl alcohol. This enzyme is believed to be a cytochrome P450 monooxygenase, and this step is believed to be the rate-limiting step in the vanillin biosynthetic pathway in cultured cells. For these reasons, up-regulation or some other form of supplementation of this enzyme in cultured cells and in intact plants.

The next key enzyme in the vanillin biosynthetic pathway is the methyl transferase that catalyzes the conversion of 3,4-dihydroxybenzaldehyde (proaldehyde) to vanillin. Though this enzyme is not believed to be rate-controlling either in cultured vanilla or in intact plants, up-regulation or some other form of supplementation of this enzyme should augment vanillin accumulation.

The next key enzyme, vanillyl alcohol dehydrogenase (VAD) actually catalyzes the destruction of vanillin rather than its synthesis. VAD is a novel enzyme found in vanilla tissue culture, but not in any significant amount in vanilla beans. The inventors have found that vanilla beans produce and accumulate vanillin as a final product, whereas in tissue culture, vanillin is produced but is converted by VAD and stored as vanillyl alcohol. Accordingly, down-regulation of VAD in cultured cells is a key feature of improved vanillin production from cultured vanilla.

In some instances it may be possible to add one or more of the above-listed enzymes directly to a vanilla cell or tissue culture, to enhance the biosynthetic activity of endogenous enzymes and increase vanillin production. However, it is preferred for practice of the present invention to augment or reduce activity of one or more of these enzymes by internal manipulation; e.g. up-regulation by genetic engineering to increase transcription or translation of endogenous genes or transgenes, or down-regulation by expression of antisense molecules or antibodies that specifically bind to genes encoding the enzymes or the enzymes themselves, respectively, or by expression of non-functional mutants, or by an overexpression/co-suppression effect.

In order to genetically manipulate the vanillin biosynthetic pathway, it is necessary to have in hand nucleic acid molecules that encode selected key enzymes of that pathway. The availability of purified or semi-purified biosynthetic pathway enzymes, as described in greater detail in the Examples, enables obtaining their encoding nucleic acid sequences by a variety of methods known in the art. Such methods can be found in general references such as Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.").

In a preferred embodiment, antibodies immunologically specific for a selected key enzyme in the vanillin biosynthetic pathway are produced, then used to screen a cDNA library made either from cultured vanilla cells or from intact plants. In an alternative embodiment, purified enzymes are partially or fully sequenced, and a set of degenerate oligonucleotide probes is produced, which encodes part or all of the sequence. These probes may be used to screen either a genomic or cDNA library by standard means or via PCR amplification.

One common formula for calculating the stringency conditions required to achieve hybridization between nucleic acid molecules of a specified sequence homology (Sambrook et al., 1989):

$$T_m = 81.5°\ C. + 16.6 \text{Log } [Na+] + 0.41(\% \ G+C) - 0.63$$
$$(\% \text{ formamide}) - 600/\#bp \text{ in duplex}$$

As an illustration of the above formula, using $[N+]=[0.368]$ and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Nucleic acids encoding vanillin biosynthetic pathway enzymes, obtained in accordance with the present invention, may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

Specific cloning strategies for the various key enzymes of the vanillin biosynthetic pathway are set forth in the Examples. Once cloned DNA is obtained, it may be used to genetically manipulate the vanillin biosynthetic pathway by enhancing or inhibiting, as appropriate, selected enzymes of the pathway.

Transgenic plants can be generated using standard plant transformation methods known to those skilled in the art. These include, but are not limited to, *Agrobacterium* vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. The biolistic DNA delivery method is useful for nuclear transformation, and is preferred for practice of the present invention. Transformation of *V. planifolia* using the biolistic method is described in detail in Example 9. In another embodiment of the invention, *Agrobacterium* vectors, particularly binary vectors such as BIN19, are used for transformation of plant nuclei.

Nucleic acids encoding vanillin biosynthetic enzymes may be placed under a powerful constitutive promoter, such as the rice actin promoter or the maize ubiquitin promoter, both of which are particularly useful for gene expression in monocots. Other constitutive promoters that may also prove useful include the Cauliflower Mosaic Virus (CaMV) 35S promoter or the figwort mosaic virus 35S promoter. Alternatively, transgenic plants expressing one or more of the genes under an inducible promoter (either their own promoter or a heterologous promoter) are also contemplated to be within the scope of the present invention. Inducible plant promoters include the tetracycline repressor/operator controlled promoter.

Using a biolistic delivery system for transformation, the coding region of interest, under control of a constitutive or inducible promoter as described above, is linked to a nuclear drug resistance marker, such as kanamycin resistance. Biolistic transformation of plant nuclei is accomplished according to the following procedure:

(1) the gene is inserted into a selected vector;
(2) transformation is accomplished by bombardment with DNA-coated microparticles, as described in Example 9;
(3) plant tissue is then transferred onto the selective medium to identify transformed tissue; and
(4) identified transformants are regenerated to intact plants or are maintained as cultured cells.

It should be recognized that the amount of expression, as well as the tissue specificity of expression of the transgenes in transformed plants can vary depending on the position of their insertion into the nuclear genome. Such position effects are well known in the art. For this reason, several nuclear transformants should be regenerated and tested for expression of the transgene.

In some instances, it may be desirable to down-regulate or inhibit expression of endogenous enzymes, such as VAD in cultured *V. planifolia*. Accordingly, VAD-encoding nucleic acid molecules, or fragments thereof, may also be utilized to control the production of VAD. In one embodiment, full-length VAD gene antisense molecules or antisense oligonucleotides, targeted to specific regions of VAD-encoding mRNA that are critical for translation, are used. The use of antisense molecules to decrease expression levels of a pre-determined gene is known in the art. In a preferred embodiment, antisense molecules are provided in situ by transforming plant cells with a DNA construct which, upon transcription, produces the antisense sequences. Such constructs can be designed to produce full-length or partial antisense sequences.

In another embodiment, overexpression of a VAD-encoding gene is induced to generate a co-suppression effect. This excess expression serves to promote down-regulation of both endogenous and exogenous VAD genes. Alternatively, transgenic plants can be created containing mutations in the region encoding the active site of the enzyme, thereby creating a pool of non-functional enzyme in the plant cells, which competes for substrate (i.e., vanillin), but is unable to catalyze the conversion to the undesired product (vanillyl alcohol).

From the foregoing discussion, it can be seen that genetic manipulation of the enzymes involved in the vanillin biosynthetic pathway will produce engineered plant tissue culture and, if desired, intact plants capable of high yield of vanillin and related compounds of value. This approach, alone or combined with the alternative approach of stimulating vanillin production in cultured cells by supplementation with elicitors or biosynthetic precursors, result in improved production of vanillin from a variety of sources, in accordance with the present invention.

The following specific examples are provided to illustrate embodiments of the invention. They are not intended to limit the scope of the invention in any way.

EXAMPLE 1

Protocol for Initiation of Vanilla Embryo Culture

Green vanilla beans (from Indonesia), 2 to 8 months after pollination, were washed with cold water, then with mild detergent and water, and were next held for 30 minutes in a water solution containing 20% bleach and a drop of Tween-80. The beans were then rinsed in sterile water and dried. Seeds from the washed beans were scraped and placed on a petri plate containing solid medium ("G-medium") as follows.

Gamborg's B-5 basal medium
2% sucrose
vitamins (see attached list)
antibiotics—cefotaxime sodium and vancomycin sodium at 100 mg/l each;
optionally, tetracycline or chloramphenicol at 50 mg/l each;
0.8% agar Beans were dissected transversely or longitudinally and the tissue containing the seeds planted on the agar.

To break seed dormancy and to accelerate germination, we applied the following:

10 ppm ethylene
100% oxygen
1–10 µM urea
1–10 µM abscisic acid
Heat shock (37° C. for 3 hours)
Cold shock (2–3° C. for 48 hours)

After 2 to 6 months, seeds germinated and were transferred to fresh agar medium. When germinating shoots reached about 10 mm, they were dissected in half and transferred to fresh agar medium. This process was repeated every two weeks for three months. The agar-cultured embryo tissue was transferred to liquid G-medium without agar. The liquid culture was maintained on an orbital shaker at 130 rpm. Embryo culture was subcultured every two weeks by collecting embryos on a sieve and dissecting the growing embryos into 2 to 4 pieces, depending on the size.

Some embryos were maintained on solid medium and some were kept on rafts (Sigma, St. Louis, Mo.). All cultures were held in light (80 µE/sec/cm) at 25–28° C.

The protocol for initiation of cell suspensions from embryo cultures of *V. planifolia* was as follows. Established embryo cultures were transferred from petri plates containing G-medium to the same medium, supplemented with 1 µM 2,4-D, then subcultured for two weeks. After callus was initiated, it was transferred to solid medium containing 0.5 µM 2,4-D. After 2 to 6 additional subcultures, the resulting soft callus was transferred to liquid G-medium with 0.5 µM 2,4-D and maintained as cell suspension.

EXAMPLE 2

Scheme for Vanillin Biosynthetic Pathway

We derived a scheme for the vanillin biosynthetic pathway by analysis of metabolites in cultured embryos and by experiments with feeding of precursors and intermediates. This scheme is shown in FIG. 1 and the experiments are described below.

Embryo cultures of *Vanilla planifolia* were established as described in Example 1. The procedures used to extract phenolics from the cultured embryo cells and to analyze the extracts by high pressure liquid chromatography (HPLC) were as described generally by Havkin-Frenkel et al., Plant Cell, Tissue and Organ Culture 45: 133–136 (1996).

In the extraction procedure, 3 ml of 0.05 M sodium acetate buffer, pH 5.5, was added to about 1 gram of fresh culture. Samples were placed in boiling water for three minutes, then chilled. The cells were next homogenized in a Polytron blender for 1 minute at medium speed. A β-glucosidase solution was added to the homogenized cells to give a final concentration of 0.2%. Each sample was then incubated at 37° C. for 5 hr. Next, 17 ml of 95% ethanol was added, after which incubation at 37° C. was continued for an additional 24 hrs. The extract was then filtered and the ethanol evaporated. The filtrate was extracted twice using ethyl acetate, then extracted twice with ethyl acetate acidified to pH 3 with HCl. The extracts were combined and the ethyl acetate evaporated. The residue was dissolved in 1 ml of acidified methanol and filtered with a 0.45 µm syringe filter for HPLC analysis.

Extractions of metabolites from culture medium was similar to the cell extraction protocol. Five ml of spent medium was incubated in a β-glucosidase solution at 37° C. for 24 hrs. The medium was then extracted with ethyl acetate and the organic portions combined and evaporated, as for the cell extracts.

Metabolite levels were measured with a Hewlett Packard 1090L or a Waters HPLC with a UV detector at 280 nm. The Waters HPLC was also equipped with a diode array detector to confirm the identities of the various intermediates, and the identities of the various intermediates were further confirmed by mass spectrometry. The column was a Supelco C-18 DB column of dimensions 250 mm×4.6 mm and a particle size of 5 µm. The mobile phase contained methanol and water, each of which was acidified with 1.25% acetic acid. The flow rate was 1 ml/min, with a solvent gradient as follows:

| Time (min) | % Water |
|---|---|
| 0–10 | 85 |
| 20–25 | 80 |
| 30–42 | 50 |
| 42–end | 85 |

HPLC analyses of tissue extracts from cultured embryos revealed threshold levels of p-coumaric acid, p-hydroxybenzoic acid and p-hydroxybenzaldehyde; usually high levels of p-hydroxybenzyl alcohol, trace levels of 3,4-dihydroxybenzyl aldehyde (Pro-ald), vanillin and vanillyl alcohol.

It is known that coumaric acid (CA) is derived from the deaminization of phenylalanine or tyrosine. The acid, a C6-C3 compound, is converted by chain shortening to p-hydroxybenzaldehyde (BA), a C6-C1 compound. Feeding experiments with CA revealed that exogenously applied CA is immediately converted to BA. We examined if benzoic acid or p-hydroxybenzyl aldehyde may be intermediates in the conversion of CA to BA, but a definitive answer has not yet been reached. However, it is clear that at least one chain shortening enzyme is involved in the conversion from CA to BA, and that this step does not appear to be rate-limiting in cultured cells. However, some evidence indicates that it is the rate-limiting step in intact vanilla beans.

A key juncture in the pathway in cultured cells appears to be the hydroxylation of HBA to 3,4-dihydroxybenzyl aldehyde or alcohol and subsequently, vanillin and vanillyl alcohol. Feeding of 3,4-dihydroxybenzyl aldehyde resulted in the rapid methylation and conversion to vanillin or vanillyl alcohol, indicating that these steps are not limiting. The constraint appears to be in the hydroxylation of HBA, for the following reasons:

1. HBA is usually found in higher levels than other intermediates, suggesting a block in further turnover of the compound.

2. Feeding of CA resulted in the accumulation of HBA but only trace amounts of other compounds.

3. Chemical stresses that induce the enzymatic turnover of HBA resulted in the disappearance of the compound and the simultaneous increase in dihydroxybenzyl alcohol or aldehyde, as well as vanillin and vanillyl alcohol.

4. In tissue homogenates where enzyme and substrate are accessible to each other, HBA was rapidly metabolized to dihydroxybenzyl aldehyde. Feeding the homogenates with HBA increased accumulation of dihydroxybenzyl aldehyde, which was the final product since methylation requires intact tissue or the addition of S-adenosyl methionine (SAM).

5. Cytochrome P450 enzymes are normally inducible enzymes that become active at certain stages of development or differentiation. Since the embryo culture is composed of undifferentiated cells, this explains why Cyt p450 activity is not observed.

Thus, our data suggest unhindered metabolite flux to and from HBA in cultured vanilla embryo cells. Hydroxylation of the compound induced by chemical or genetic means is expected to lead to augmented production of vanillin and related compounds in cultured cells.

EXAMPLE 3

Use of Vanilla Tissue Culture for the Bio-Conversion of 3,4-Dihydroxybenzaldehyde to Vanillin and Vanillyl Alcohol The following procedure was used for the bio-conversion of 3,4-dihydroxybenzaldehyde ("proaldehyde") to vanillin and vanillyl alcohol in *V. planifolia* tissue culture. The medium used for cultures was G-medium as described above. Pro-ald solutions were prepared in G-medium, to final concentrations of 0.01 to 5 mM.

Cultures used for the bio-conversion were (1) clusters, (2) embryo culture, and (3) tissue homogenates of the above cultures. Cultures were of varying ages ranging from 0 to 1 month old. The cultures were allowed to remain under normal culture conditions for 0 to 15 days. As controls, untreated cultures were extracted and analyzed as described in Example 2.

Proaldehyde at different concentrations was added to the medium, either alone or in combination with the following treatments:
- malic acid (0.01–3.0%)
- varying pH of the medium
- varying ascorbic acid concentration
- varying temperatures, including cold and heat.

Bioreactor-grown cultures were used for the bio-conversions. Different kinds of impeller designs were used to increase or decrease shear stress on the cells prior to the addition of pro-ald. As shown in Example 5, it was found that addition of 1–5 mM pro-ald increased the production of vanillin/vanillyl alcohol by several hundred fold.

In another experiment, the effect of daily refreshing of the pro-ald containing culture medium was examined. Cultures were transferred to medium containing 5 mM pro-ald. Control cultures were left in this medium for the duration of the experiment. For test cultures, the medium was removed daily and replaced with fresh medium containing pro-ald. Cultures subjected to this daily medium change were improved in their appearance and growth, as compared with cultures remaining in the same medium.

EXAMPLE 4

Malic Acid-Induced Vanillin and Vanillyl Alcohol Production

Application of malic acid to vanilla tissue culture induced the production/accumulation of vanillin and vanillyl alcohol. Malic acid in concentrations of 0.1 to 3% was applied as a disodium salt to the growing medium. The culture was maintained for 1 to 15 days, then was extracted as described in Example 2. Results are shown in Table 6 in the following example.

Malic acid was applied to the following: (1) intact roots, (2) intact shoots, (3) embryo cultures, (4) cluster cultures, and (5) cuttings. The age of the cultures were between 0 and 1 month. Malic acid was applied alone or in combination with the following: starvation without sugar (sucrose); shear stress induced by bioreactor impeller; citric acid; varying concentrations of oxygen and ethylene; oxaloacetic acid (sodium salt); ascorbic acid; pyruvic acid; glutamic acid; succinic acid; or salt stress.

Adding proaldehyde for a few days, followed by addition of malic acid, was found to increase production of vanillin and vanillyl alcohol. If sucrose is omitted from the malic acid treatment (i.e. starvation due to lack of sucrose), the onset of vanillyl alcohol production occurs more quickly.

Shear stress had a significant effect on vanillin production. The bioreactor with a marine impeller (5 liters, 110–120 rpm, airspeed 250 ml/min) was used to culture embryo and cluster cultures for about 21 days. Addition of malic acid after this time resulted in the highest production of vanillin and vanillyl alcohol.

EXAMPLE 5

Results of Selected Feeding Experiments

Results of selected experiments in which precursors or elicitors were added to vanilla cultures are set forth below. These experiments were performed in accordance with the procedures set forth in Examples 1–4. The following abbreviations are used:

CA or PC=p-coumaric acid

HY=p-hydroxybenzoic acid

BA=p-hydroxybenzaldehyde

HBA=p-hydroxybenzyl alcohol

Pro-ald=3,4-dihydroxybenzaldehyde

HMBA and Vn. Alc.=vanillyl alcohol

Vn=vanillin

FA=ferulic acid

CAF=caffeic acid

The table below shows results of experiments in which vanillin precursors were fed to vanilla embryo cultures.

TABLE 1

Feeding Vanilla Embryo Culture with Vanillin Precursors (mg/100 g dry wt.)

| PRECURSORS | CA | HBA | PRO-ALD | VN ALC | VN |
|---|---|---|---|---|---|
| CONTROL | 108 | 9300 | 13 | 53 | 0.01 |
| CA (1 mM) | 220 | 13000 | 10 | 10 | 0.01 |
| FA (25 mM) | 136 | 11007 | 4.8 | 23.8 | 11.8 |
| CAF (2 mM) | 189 | 11350 | 21 | 32 | 0.5 |
| BA (1 mM) | 125 | 10305 | 5.8 | 12.3 | 0.015 |
| HBA (1 mM) | 158 | 13100 | 4.6 | 9.6 | 0.001 |
| PRO-ALD (1 mM) | 285 | 8950 | 433 | 286.8 | 16.7 |
| VN. ALC. (2 mM) | 206 | 10350 | 1.1 | 882 | 8.5 |

In an experiment with intact plant material, whole green vanilla beans (6 months post-pollination) were infiltrated with various vanillin precursors. The precursors (1.0 mM each in 0.1 M mannitol) were infiltrated by submerging the beans under vacuum into the solutions for 15 minutes, removing and drying the beans, then measuring amounts of precursors daily, for 5 days. The table below shows the results of one such experiment.

TABLE 2

Feeding green vanilla beans with vanillin precursors

| PRECURSOR | CA | BA | HY | HBA | PRO-ALD | Vn | Van. Alc |
|---|---|---|---|---|---|---|---|
| CA | + | | | ++ | ++ | ++ | |
| BA | | ++ | | | | | |
| HY | | | ++ | | | | |
| HBA | −+ | | | ++ | ++ | ++ | |
| PRO-ALD | | | | | ++ | +++ | |

TABLE 2-continued

Feeding green vanilla beans with vanillin precursors

| PRECURSOR | CA | BA | HY | HBA | PRO-ALD | Vn | Van. Alc |
|---|---|---|---|---|---|---|---|
| Vn | | | | | | +++ | |
| Van Alc | | | | | −+ | | +++ |

The table below shows the results of experiments in which *Fusarium* cell walls were added to vanilla embryo cultures as an elicitor of vanillin production. The results show that *Fusarium* cell walls stimulate production of various precursors of vanillin, up to the apparently rate-limiting step of HBA to pro-ald.

TABLE 3

Effect of Fusarium Cell Wall on Flavor Production in *Vanilla planifolia* Embryo Culture

| | mg/100 g Dry Weight | | | |
|---|---|---|---|---|
| TREATMENT/COMPOUND | HBA | HY | BA | PC |
| Control/No Additions | 3700 | 35 | 65 | 52 |
| 27 mg. dry cell wall | 4300 | 50 | 67 | 127 |
| 50 mg. dry cell wall | 6700 | 128 | 198 | 389 |

Culture conditions: Cells were grown for 2 days at 28° C. at 180 RPM

The table below shows the results of experiments testing the effect of chilling temperature on vanillin precursors in vanilla cluster cultures. These results indicate that chilling stress stimulates production of vanillin precursors, up to the rate-limiting conversion of HBA to pro-ald.

TABLE 4

Effect of Chilling Temperature on Vanillin Precursors in *Vanilla planifolia* Cluster Culture

| | mg/100 g Dry Weight | | | |
|---|---|---|---|---|
| | HBA | HY | BA | PC |
| 15 Hrs. at 13° C. | 144.0 | 2.1 | 15.9 | 7.2 |
| 15 Hrs. at 13° C. 17 Hrs. at 28° C. | 232.0 | 1.8 | 26.4 | 7.4 |
| 15 Hrs. at 13° C. 7 Days at 28° C. | 586.0 | 7.4 | 52.4 | 15.7 |
| Control 7 Days at 28° C. | 111.0 | 0.74 | 20.3 | 5.5 |

The table below shows the results of experiments testing the effect of glycosylated lysozyme, an elicitor protein described in U.S. Pat. No. 5,552,307 on vanillin precursors in vanilla embryo cultures. As can be seen, these proteins were effective in stimulating vanillin production in the cultured cells.

TABLE 5

Effect of Elicitor Protein on Vanillin Precursors in *Vanilla planifolia* Embryo Cultures

| | mg/100 g Dry Weight | | | | | | |
|---|---|---|---|---|---|---|---|
| Treatment/Compound | HBA | HMBA | PROALD | HY | BA | VN | CA |
| Control/No Addt | 1990.8 | 38.1 | 9.7 | 76.0 | 77.7 | 3.6 | 151.0 |

TABLE 5-continued

Effect of Elicitor Protein on Vanillin Precursors in *Vanilla planifolia* Embryo Cultures

| | mg/100 g Dry Weight | | | | | | |
|---|---|---|---|---|---|---|---|
| Treatment/Compound | HBA | HMBA | PROALD | HY | BA | VN | CA |
| 30 µg/ml Elicitor Protein Added | 20006.3 | 30.7 | 137.0 | 83.4 | 79.7 | 8.4 | 152.0 |

Each point represents an average of 5 flasks.
Culture conditions: Cells were grown for 7 days at 25° C. at 180 RPM The table below shows the results of HPLC analysis of intermediary metabolites induced by malic acid elicitation in embryo culture and grown under standard conditions, respectively. Cultures were grown in medium containing 3% malic acid by weight, for 7 days. These results show that malic acid stimulates vanillin production in embryo cultures more than tenfold.

TABLE 6

HPLC Analysis of Intermediary Metabolites Induced by 3% Malic Acid in *Vanilla planifolia* Embryo Culture

| Growth conditions | HBA | VN | HMBA | PROALD | BA | HY | PC |
|---|---|---|---|---|---|---|---|
| | (Percent of Dry Weight) | | | | | | |
| Standard | 11.07 | 0.005 | 0.023 | 0.024 | 0.03 | 0.053 | 0.20 |
| Malic Acid | 3.60 | 0.072 | 0.700 | 0.025 | 0.02 | 0.050 | 0.20 |

EXAMPLE 6

Figure 2:
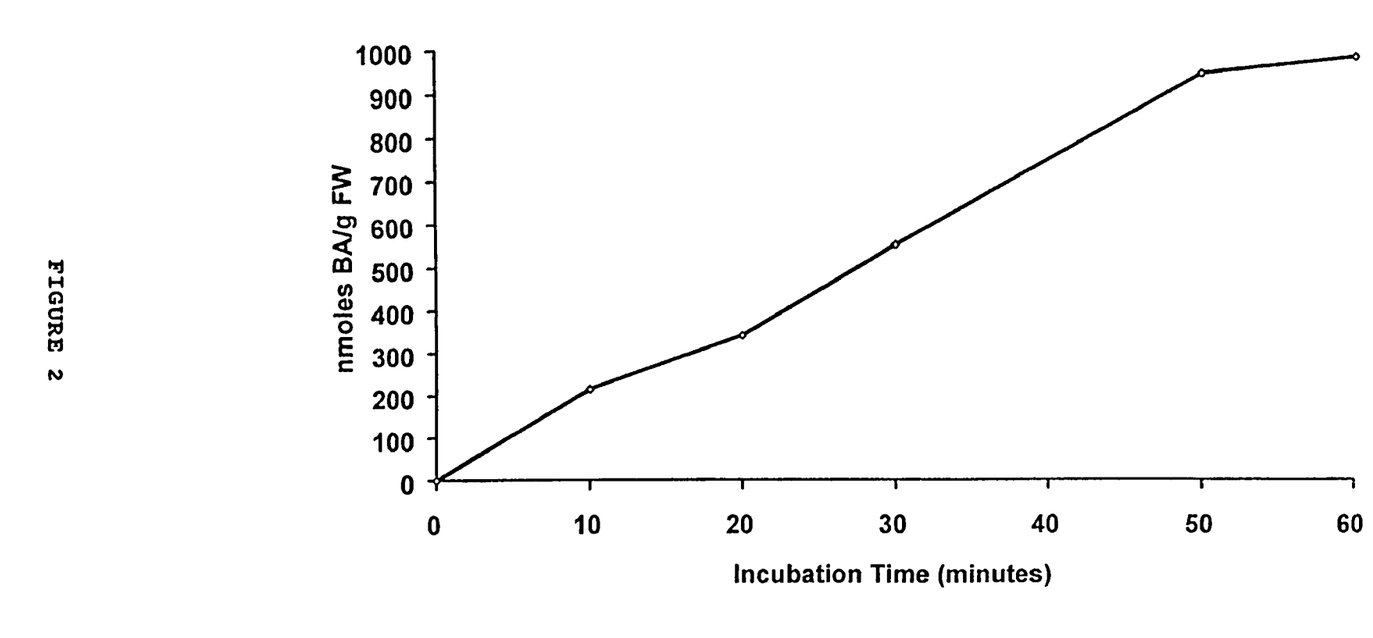
FIG. 2. Graph showing the conversion of p-coumaric acid to p-hydroxybenzaldehyde as catalyzed by p-hydroxybenzaldehyde synthase in *V. planifolia* embryo culture.

Purification and Characterization of Hydroxybenzaldehyde Synthase from *Vanilla planifolia* Green Embryo Culture Conversion of p-coumaric acid to p-hydroxybenzyl alcohol in vanilla is catalyzed by at least one chain-shortening enzyme. The rate of conversion as catalyzed by this enzyme is shown in FIG. 2. Characteristics of p-coumaric acid chain shortening enzyme, also referred to as hydroxybenzaldehyde Synthase, are described in this example. It should also be noted that ferulic acid is converted to vanillin by one or more other chain shortening enzymes, which are believed to be distinct from the p-coumaric acid chain shortening enzyme.

Plant Material

Figure 3:
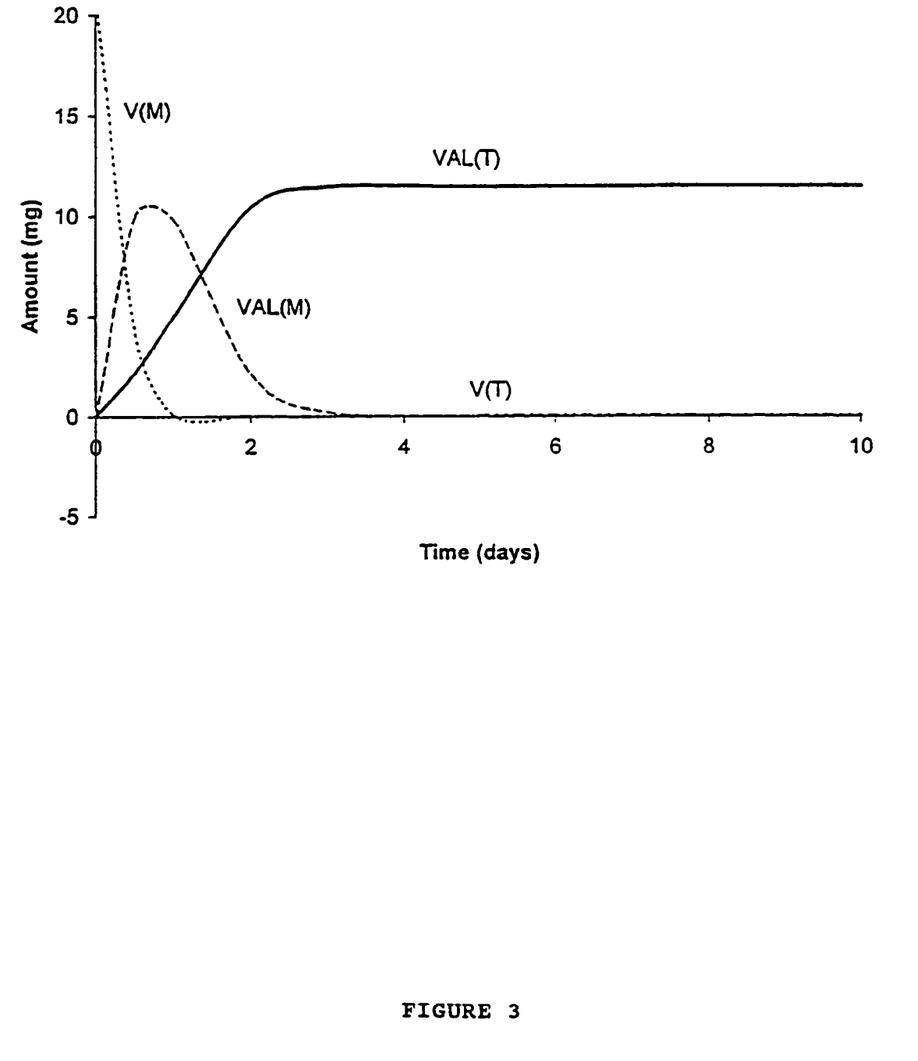
FIG. 3. Graph showing uptake of exogenously added vanillin and its transformation to vanillyl alcohol by vanillyl alcohol dehydrogenase in *V. planifolia* embryo culture. V(T)=vanillin in tissue; V(M)=vanillin in medium; VAL(T) =vanillyl alcohol in tissue; VAL(M)=vanillyl alcohol in medium.

The embryos were cultivated on sterile Gamborg B-5 liquid medium (3% inoculum) containing microelements, vitamins, supplemented with 2% of sucrose. The culture was grown at room temperature, under constant illumination (2× OSRAM-DULUX El GLOBE, 100 W each) on rotary shaker (150 rev./min) and subcultured every 3–4 weeks. The conversion of p-coumaric acid to p-hydroxybenzaldehyde as catalyzed by the enzyme(s) is shown in FIG. 3.

Crude Enzyme Extraction

Sterile plant material (2 g) 2–3 weeks after subculture, was homogenized in a cooled Potter glass homogenizer with 4 ml of 0.1 M HEPES buffer, pH 8.0, containing 10 mM DTT. The homogenate was next centrifuged at 4° C. at 15.000× g for 15 min. Resultant supernatant (4 ml) was filtered through Sephadex G-25 column (void volume 3–4 ml.) Equilibrated with Tris/HCL buffer pH7, containing 10 mM DTT. The column was washed with the same buffer and 2 ml fraction following the void volume was collected. This fraction was used as the crude enzyme source.

The crude enzyme was subjected to SDS polyacrylamide gel electrophoresis. A major band was observed at about 150–200 kDa.

Determination of the Enzyme Activity

The p-HO-aldehyde synthase activity was determined in the following mixture:

crude enzyme extract: 10 µl substrate 100 µl (substrate=1.8 mM p-coumarate in 0.1 M Tris/HCl, pH 8.0 with 10 mM DTT)

The mixture was incubated for 10–60 min (for longer incubation times, the activity was not proportional with time) at 35° C. and next, the reaction stopped by addition of 200 µl of acidified methanol (10% acetic acid in methanol). The slurry was passed through 0.45 µm filter and the filtrate (50 µl) injected into HPLC Bio-sil 18 HL 90-5 column (Reversed phase, 250 mm×4.6 mm). The HPLC column mobile phase was methanol: water (15:85) acidified with acetic acid (1.25%) at flow rate 1 ml/min. The eluate was monitored at 280 nm and retention time of the reaction product was compared to retention time of the standard compounds (benzaldehyde, p-HO-benzaldehyde, vanillin, protocatechuic aldehyde, p-coumaric acid, caffeic acid, ferulic acid, coniferyl aldehyde). The results were quantified using LKB Bromma 2221 Integrator.

TABLE 7

Enzymatic Activity of Crude Preparation of p-hydroxybenzaldhyde synthase from *V. planifolia*

| Incubation time (min) | activity (nmoles of P-HO-benzaldehyde/g.fr.wt./hr) |
| --- | --- |
| 10 | 215 |
| 20 | 342 |
| 50 | 946 |
| 60 | 984 |
| 120 | 1022 |

Optimum pH

Extraction efficiency was checked for pH condition from 3 to 9 using citrate and Tris buffers. A broad optimum was found with maximum at pH 8.0. The enzyme pH optimum activity was located between pH 7 and pH 9 and corresponded to optimum of the enzyme extraction.

TABLE 8

Effect of pH of Extraction on Enzymatic Activity

| pH of extraction | activity (nmoles/gfw/h) |
| --- | --- |
| 3 | 199 |
| 4 | 214 |
| 5 | 258 |
| 6 | 306 |
| 8 | 350 |
| 9 | 205 |

TABLE 9

Effect of pH of Reaction on Enzymatic Activity

| pH of reaction | activity (nmoles/gfw/h) |
| --- | --- |
| 4 | 29 |
| 5 | 29 |
| 7 | 171 |
| 8 | 548 |
| 9 | 479 |

Stability of the Crude Enzyme Preparation

Samples of the G-25 Sephadex filtered enzyme were stored up to 11 days at 5° C. and frozen at minus 17° C.:

TABLE 10

Stability of Crude Enzyme Preparation

| Days of storage | 5° C. % of activity | −17° C. % of activity |
| --- | --- | --- |
| 0 | 100 | 100 |
| 1 | 55 | 60 |
| 4 | 30 | 41 |
| 6 | 27 | 34 |
| 11 | 0 | 20 |

Ammonium Sulfate Fractionation

HEPES pH 8.0 enzyme extract was subjected to ammonium sulfate fractionation (Salt grinded into fine powder, ice bath).

TABLE 11

Activity in Various Ammonium Sulfate Fractions

| Amm. Sulf. % saturation | Protein content (µg) | total activity (nmol/h) | sp. activity (mnol/mg/hr) |
| --- | --- | --- | --- |
| control | 7100 | 7800 | 1098 |
| 0–30 | 4800 | 465 | 97 |
| 30–60 | 450 | 4710 | 10466 |
| 60–95 | 100 | 3510 | 35100 |

These results demonstrate no loss in recovery of total activity and about 35× purification in fraction precipitated between 60 and 95% ammonium sulfate saturation.

Substrate Specificity

As a potential substrates for chain shortening enzyme the following compounds were tested:

TABLE 12

Substrate Specificity of p-hydroxybenzaldehyde Synthetase

| Compound | Expected product | Result |
| --- | --- | --- |
| t-cinnamic acid | benzaldehyde | negative |
| p-coumaric acid | p-HO-benzaldehyde | positive |
| caffeic acid | protocatechuic aldehyde | negative |
| ferulic acid | vanillin | negative |
| 4-HO-3-metoxycinnamyl aldehyde (coniferyl aldehyde) | vanillin? | negative |

These results indicate very high specificity of the tested enzyme towards p-coumaric acid.

EXAMPLE 7

Strategies for Cloning a cDNA Encoding the Cyt P450 Monooxygenase that Catalyzes the Rate-Limiting Step in Vanillin Biosynthesis I. PCR-Based Method One object of the present invention is the cloning of the cytochrome P450 that catalyzes the 3-hydroxylation of p-hydroxybenzyl alcohol. Although the activity of this enzyme is apparent from the precursor feeding studies described above, the general lability and low abundance of plant cytochrome P450 enzymes probably rules out cloning by classical enzyme purification. Therefore, an alternative strategy is to use a polymerase chain reaction (PCR) based method, using RNA isolated from a system in which the enzyme activity is highly induced, namely vanilla cell cultures exposed to an elicitor, such as malic acid. This strategy is facilitated by the recent appearance of many plant P450 sequences in the gene data bases, as this allows the design of primers that can be used for PCR amplification of unknown P450 sequences. According to the latest review on plant cytochrome P450s, ninety different sequences have been listed that appear to encode such enzymes. However, most of these have no known function as yet.

The genes encoding cytochrome P450s are highly divergent at the nucleotide sequence level. Nevertheless, these enzymes do contain conserved sequence motifs in their open reading frames sufficient for the design of PCR-based cloning strategies. Specifically, a highly conserved motif (F-G-R-C-G), that includes the cysteine residue which binds the heme group necessary for catalysis by this class of enzyme, is present in all known P450s, and is located near the carboxyl end of the protein. Forward and reverse oligonucleotide primers are constructed for PCR amplification. These are based on sequence motifs surrounding nucleotides 500, 1050, and 1400 (the heme binding region) of the alfalfa cinnamate 4-hydroxylase cytochrome P450, one of the best characterized plant cytochromes P450. Degenerate primers are constructed. In particular, inclusion of each of the 4 nucleotides (A, T, G, C) at the 3 end, optimizes the amplification of novel P450 sequences. The PCR primers also contain restriction endonuclease sites at their ends to facilitate cloning of the PCR products.

The template for PCR amplification, as described above, is double-stranded DNA produced by reverse transcription of RNA from vanilla cell culture exposed to an elicitor, such as malic acid. After separation of PCR products by gel electrophoresis, the amplified band containing multiple P450s is cut out from the gel, and cloned into *E. coli*. The inserts in individual clones are analyzed by gel electrophoresis to determine insert size, followed by restriction enzyme analysis in order to place the clones into classes. Central to our experimental design, we then use the various P450 inserts as labeled probes for northern blot hybridization to RNA isolated from elicited and unelicited cultures. P450s that are present in the elicited but not the unelicited culture are taken to the final stage of the analysis, the functional expression for enzymatic activity.

Initially, the P450s will be expressed in *E. coli*. For such a method to be successful, it is usual to co-express, in trans, a NADPH cytochrome P450 reductase. This could be from various sources, but the P450 reductase from the bacterium *Pseudomonas*, or the plant *Arabidopsis* is used initially. Enzymatic assay in bacteria is facilitated by a staining method for colonies expressing an enzyme capable of forming ortho-dihydroxyphenols, as described by Yabannavar and Zylstra (1995). In an alternative strategy, the DNA is expressed in yeast, using the pYEUra3 expression vector that has been successfully used for yeast expression of the alfalfa cinnamate 4-hydroxylase P-450 (Fahrendorf and Dixon, 1993).

Once cloned and expressed, the cyt P450 that catalyzes the hydroxylation p-hydroxybenzyl alcohol to 3,4-dihydroxybenzyl alcohol is further analyzed in order to determine its substrate specificity. For example, is the enzyme promiscuous in its specificity, or does it only hydroxylate p-hydroxybenzyl alcohol.

The 3-hydroxylase cDNA is cloned into a suitable expression vector for vanilla transformation. Initially, the cDNA is expressed constitutively, driven by the rice actin or the maize ubiquitin promoters. These promoters are very effective in monocots. Transformation of vanilla is described in detail in a later Example.

II. Use of Auxotrophs

A major technical problem in the isolation of a particular plant gene is the method of screening cloned libraries containing many thousands of DNA or cDNA sequences for the one desired gene sequence. Recently, the method of functional complementation has been applied to the screening of libraries of cloned eukaryotic cDNA sequences. While this is one of the many technologies of gene isolation, it is particularly appealing in its power and simplicity. In this method, a mutant bacterial strain with a selectable phenotype is transformed with a higher plant cDNA library which carries full-length copies of messenger RNA molecules in the expressible form. The desired cDNA sequences are actually selected in this method, which is more powerful than screening methods in finding very rare sequences in the library. For example, mutations resulting in nutrient auxotrophies in the test bacteria have been readily used to identify the homologous gene from higher plants. The test bacteria can only grow and form colonies if they have received the homologous gene from the library which restores their nutritional deficiency. However, this method is not limited to mutant bacterial strains alone. Indeed, any selectable phenotype can be used for the complementation test and a wide variety of test organisms are possible. The best selectable phenotype is growth of the test cells. In the case of HBA-hydroxylating activity, a test strain may only be able to use HBA as a carbon source if this substance is first hydroxylated. For example, recently, the pathway of HBA metabolism has been studied in the fungus *Aspergillus fumigatus* (ATCC 28282) as part of the metabolism of p-cresol. The data indicate that HBA metabolism requires the hydroxylation by a monooxagenase enzyme for further metabolism. As this organism grows on p-cresol as a sole source of carbon and energy, the development of a mutant strain suitable for complementation testing for a plant HBA monooxagenase activity is expected to be successful. In this instance, cDNA clones encoding higher plant HBA-hydroxylating enzymes, such as the enzyme involved in the vanillin biosynthetic pathway, are cloned by selecting for microorganisms that are capable of growth on medium containing HBA as the sole carbon source.

EXAMPLE 8

Purification and Characterization of Vanillyl Alcohol Dehydrogenase (VAD), Cloning of VAD-Encoding cDNA and Gene, and Regulation of VAD Gene Expression Application of vanillin to the growing medium of embryo culture results in the rapid uptake and reduction of the applied compound to vanillyl alcohol as illustrated in FIG. 3. Further more, application of 3,4-dihydroxy-benzaldehyde, a vanillin precursor also results in the accumulation of vannilyl alcohol indicating that the tissue has high capacity for the reduction of vanillin to produce vanillyl alcohol. Similarly, vanilla embryo culture that can be elicited by various elicitors to produce vanillin accumulates vanillyl alcohol as a final product. It is important to state at this stage that all the intermediates in the pathway are found mainly as glucosides.

We have purified and characterized the activity of VAD that catalyze the reduction of vanillin to vanillyl alcohol. The enzyme was identified as an NADH or NADPH-dependent alcohol dehydrogenase. The purification protocol was as set forth below.

Crude enzyme extract: Tissue was homogenized in 0.05 M actetate-Na buffer pH 4.0 (in proportion, 1 g of the tissue and 5 ml of the buffer) in an ice bath, using Polytrone homogenizer, at 20,000 revolutions of the blade per min. The homogenate was centrifuged at 13000 g for 15 min at 4° C. and the supernatant served as the crude enzyme source.

Ammonium sulfate fractionation and molecular sieving: Crude enzyme extract (100 ml) was supplied with ammonium sulfate in an ice bath up to 60% of saturation (44.4 g of Ammonium sulphate per 100 ml). The precipitate was centrifuged and discarded. The supernatant was supplied with ammonium sulfate up to 90% of saturation (total 64.6 g per 100 ml of crude extract). The precipitate was collected (10 min centrifugation at 10,000 g), dissolved in 7 ml of extraction buffer and subjected to molecular sieving at Sephacryl S-300 High Load Column (LKB Pharmacia) 2.6×60 cm, in 0.1 M pH 4.0 acetate-Na buffer. The flow rate was adjusted to 1 ml/min and 5 ml fractions were collected. The protein elution profile was monitored at 280 nm. Five fractions (of a total of 50) containing dehydrogenase activity (130–155 ml of the column eluate) were collected.

Affinity chromatography on Red Sepharose CL 6B(LKB-Pharmacia): The active combined fractions from the Sephacryl column (24 ml) were applied on 2.5×3 cm Red Sepharose CL 6B column, equiluibrated with 0.05 M pH 4.0 acetate-Na buffer. The column was developed with 0.5 M Tris/HCL buffer pH 7.4 in 0.0–1.0 M NaCl gradient (total gradient volume—70 ml) and 2.5 ml fractions were collected. Vanillyl alcohol dehydrogenase was released from the column between 0.3–0.4 M NaCl. Fractions containing VAD activity were dialysed overnight against 0.05 M caetate-Na buffer pH 4.0 and concentrated up to 50 times using Minicon concentrating filters (Amicon).

Polyacrylamide Gel Electrophoresis: Concentrated enzyme extract was used for native and SDS polyacrylamide gel electrophoresis. In native electrophoresis, two active bands (corresponding to protein bands localized with Coomassie brilliant blue of molecular weight between 43 and 67 kDa were found. SDS electrophoresis revealed 3 still active protein bands—of 20 kDa, 37 kDa and 40 kDa.

The pH optimum for the enzyme extraction was at 3.0 and optimum activity was obtained at pH 4.0. The subunit molecular weight determined on the basis of electrophoretic mobility in the presence of SDS was around 43 kDa. Table 13 indicates that VAD shows preference toward $C_6$–$C_1$ phenolic compounds and no activity toward $C_6$–$C_3$ phenolics. 3,4-dihydroxy-benzaldehyde and vanillin appear to be the most preferred substrates while affinity to other $C_6$–$C_1$ aldehydes or acetaldehyde is lower.

TABLE 13

Substrate specificity of alcohol dehydrogenase from *Vanilla planifolia* embryo culture.

| | Activity (nmoles · gfwt$^{-1}$ · min$^{-1}$) | |
|---|---|---|
| Substrate | NADH | NADPH |
| 1. Acetaldehyde | 0.26 | — |
| 2. Benzaldehyde | 0.33 | 0.18 |
| 3. 4-hydroxybenzaldehyde | 0.32 | 0.14 |
| 4. 3,4-dihydroxybenzaldehyde | 1.89 | 2.11 |
| 5. 4-hydroxy-3-methoxybenzaldehyde | 1.26 | 0.97 |
| 6. 4methoxy-3-hydroxybenzaldehyde | 0.00 | 0.00 |
| 7. 4-hydroxy-3-ethoxybenzaldehyde | 0.42 | — |
| 8. 4-methoxy-3-ethoxybenzaldehyde | 0.00 | — |
| 9. Cinnamylaldehyde | 0.00 | — |
| 10. 4-hydroxy-3-methoxycinnamylaldehyde | 0.00 | — |

Sequence information from the purified VAD protein is used to design primers to clone the gene encoding VAD, and the cloned gene is used for the creation of a VAD antisense gene using established methods (below). Vanilla tissue culture is transformed with the antisense gene and the tissue assessed for an expected attenuation in the activity of VAD and a corresponding reduction in vanillyl alcohol accumulation concomitant with an increase in the level of vanillin.

Sequencing of the VAD Protein

The purified VAD is purified further to homogeneity, using conventional chromatographic approaches such as chromatofocusing and hydrophobic interaction chromatography. Tryptic peptides from the purified protein are sequenced by automated Edman degradation and used to design oligonucleotide primers for PCR amplification (He and Dixon, Arch. Biochem. Biophys. 336: 121–129, 1996). Since the relative position of the tryptic fragments in the VAD sequence may not be known, degenerate oligonucleotide primers based on regions of minimal degeneracy in the genetic code are designed for each peptide in both forward and reverse orientations, and the various primer combinations evaluated. Oligonucleotide sequences are synthesized as outlined by He and Dixon (1996).

Cloning of the VAD Gene

Production of cDNA Library. High levels of VAD are produced constitutively in vanilla embryo culture. Embryo culture cells are harvested on nylon mesh, frozen in liquid N2, and stored at −70 C. A cNDA library for DNA probing and expression is constructed from poly(A)+ RNA extracted from vanilla embryo culture cells using the LambdaZAP system.

PCR screening. Template DNA for PCR amplification is obtained by boiling a portion of a vanilla cDNA library as previously described (Junghans et al., Plant Mol. Biol. 22: 239–253, 1993). Amplified fragments are cloned, and sequenced to check that they contain sequences corresponding to one or more of the cryptic peptides, along with sequence diagnostic for dehydrogenases. The Lambda ZAP cDNA library from vanilla tissue are autoexcised into p-Bluescript, and screened with PCR fragments that had been 32-labeled by random priming. Positive plaques are identified by autoradiography. Full length clones are sequenced on both strands, and functional identification is performed by expression in E. coli.

Immunoscreening. In another approach the expression library containing cDNAs derived from transcripts from vanilla embryo culture cells are screened with an antiserum raised against VAD. E. coli (XL-1 Blue cells obtained from Stratagene) are infected with the library, and positive clones selected be purified by several rounds of screening and processed to homogeneity. Sequencing of VAD cDNA clones is according to standard methods.

Regulation of Expression

Expression of VAD in Vanilla Tissues and Cell Cultures. The expression pattern of VAD in vanilla beans and embryo cultures is determined by northern blot hybridization, and the genomic organization of VAD determined by Southern blot hybridization. RNA is extracted as previously described (Logemann et al., Anal. Biochem. 163: 16–20, 1987), total RNA separated and transferred to and fixed onto cellulose membranes (Jorrin and Dixon, Plant Physiol. 92: 447–455, 1989) and hybridized to an internal coding fragment of VAD. Genomic DNA is isolated from vanilla culture, digested with restriction enzymes, fractionated by electrophoresis and hybridized to a labeled VAD using standard procedures.

Antisense. Double stranded full length VAD clones are sequenced in both directions and used to construct a VAD antisense gene.

Transformation of Vanilla Cultured Cells with VAD Antisense Constructs. The VAD cDNA is cloned, in both sense and antisense orientations, into a suitable expression vector for vanilla tissue transformation. The idea is that some sense transformants may exhibit highly reduced VAD activity due to epigenetic co-suppression. Initial transformations focus on achieving constitutive expression driven by the rice actin or the maize ubiquitin promoters. The cDNA clone is introduced by particle bombardment as described in a later Example.

Analysis of Transgenic Plants. Putative transgenic plants are screened for the VAD antisense transgene by PCR using primers designed to sequences within the selectable marker gene. Transformation is confirmed by Southern border analysis using a VAD cDNA probe. Screening for expression of VAD activity in transformed vanilla culture is done spectrophotometrically based on NADH oxidation as previously described (Biscak et al., Arch. Biochem. Biophys. 215: 605–615, 1982, Longhurst et al., J. Food Biochem. 14: 421–433, 1990) and VAD transcripts determined by northern blot hybridization. In addition, the culture is extracted and analyzed by HPLC for the intermediates in the vanillin biosynthetic pathway (Havkin-Frenkel et al., 1996), in particular the levels of vanillin and vanillyl alcohol. The enzyme (VAD) is extracted as described above.

EXAMPLE 9

Transformation of Vanilla planifolia

Cultured Vanilla planifolia was transformed by the procedure set forth below:

1. Vanilla culture was grown on a basic medium agar plates containing 2,4 dichloro-phenoxyacetic acid (2,4-D), was subcultured 3 times during 4 months according to the procedures described above. Cultures were kept at 25° C., 15% humidity, under illumination of 80 µE/sec/m².

2. Soft callus from the culture was chopped to very small pieces.

3. The pieces were washed with regular (basic) liquid media (G medium as described above) and transferred to agar plates containing basic media plus 1% polyvinylpyrrolidone (PVP) and to plates containing basic media plus 1% charcoal.

4. The green pieces from each plate were washed every day for 5 days and transferred to new PVP/charcoal plates.

5. Only the green pieces were collected and placed on a disk in a basic medium plus 0.6 M mannitol agar plates for 4 hours.

6. Particle bombardment was done according to standard methods, using ACT 1 D plasmid (McElroy et al., Plant Cell 2: 163–171, 1990) having the rice actin promoter fused to a beta-glucoronidase "GUS" coding sequence.

The gun used was a Biored PDS 1000/He Biolistic Delivery System, used at 11,000 psi at a distance of about 10 cm. The samples were kept over night after bombardment.

7. The samples were transfered to a basic media agar plates for 24 hours.

8. The tissue samples were stained for "GUS" activity using X/Gluc, and incubated at 37° C. over night.

Results of GUS staining demonstrated that the vanilla tissue had taken up the plasmid and were able to express GUS. This indicates a successful transformation of vanilla callus tissue using the above-described procedure.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing vanillin in cultured Vanilla planifolia, which comprises:
   a) providing a tissue culture of said Vanilla planifolia;
   b) supplementing the culture with a compound selected from the group consisting of malic acid at a concentration of about 3% by weight of the culture medium, 1 mM 3,4-dihydroxybenzaldehyde, and 30 µg/ml glycosylated lysozyme; and
   c) culturing the Vanilla planifolia in the presence of the compound, thereby producing vanillin.

2. The method of claim 1, wherein the tissue culture is an embryo culture.

3. A method for producing vanillin in cultured Vanilla planifolia, which comprises:
   a) providing a tissue culture of said Vanilla planifolia;
   b) subjecting the culture to mechanical shear stress for 21 days; and
   c) adding malic acid at a concentration of between about 1% and 3% by weight of the culture medium.

4. The method of claim 3, wherein the culture is supplemented with 3,4-dihydroxybenzaldehyde at a concentration of between about 0.1 and 5 mM.

5. The method of claim 3, wherein the culture is supplemented with about 0.01 to about 5% by weight of a compound selected from the group consisting of succinic acid, oxaloacetic acid, citric acid and pyruvic acid.

6. The method of claim 3, wherein the culture is supplemented with about 30 µg/ml of glycosylated lysozyme.

7. A cell culture comprising Vanilla planifolia cells in a culture medium supplemented with an elicitor of vanillin synthesis selected from the group consisting of malic acid at 0.1–3% by weight, 1 mM 3,4-dihydroxybenzaldehyde, and glycosylated lysozyme at about 30 μg/ml, wherein, after about 15 days exposure to the elicitor, the cell culture produces at least twice as much vanillin as a cell culture after 15 days in culture under equivalent conditions, in a culture medium which was not supplemented with the elicitor.

8. The cell culture of claim 7, which, after 15 days exposure to the elicitor, produces at least ten times as much vanillin as a cell culture after 15 days in culture under equivalent conditions, in a culture medium which was not supplemented with the elicitor.

9. The cell culture of claim 7, wherein the cells are embryo cells.

10. The cell culture of claim 7, wherein the cells are root cells.

11. The cell culture of claim 7, which, after 7 days exposure to the elicitor, produces at least ten times as much vanillin as a cell culture after 7 days in culture under equivalent conditions, in a culture medium which was not supplemented with the elicitor.

* * * * *